United States Patent [19]

Sugahara et al.

[11] Patent Number: 5,599,327
[45] Date of Patent: Feb. 4, 1997

[54] CONNECTOR

[75] Inventors: Michihiro Sugahara; Toshinobu Ishida, both of Kanagawa-ken, Japan

[73] Assignee: Terumo Kabushiki Kaisha, Tokyo, Japan

[21] Appl. No.: 357,336

[22] Filed: Dec. 16, 1994

[30] Foreign Application Priority Data

Dec. 16, 1993 [JP] Japan .................................. 5-317109

[51] Int. Cl.$^6$ ............................................. A61M 25/00
[52] U.S. Cl. ............................................. 604/283; 604/167
[58] Field of Search ................................... 604/167, 169, 604/164, 905, 165, 256, 283, 280, 284, 326, 246, 250, 249; 251/149.1; 137/849; 285/95, 109

[56] References Cited

U.S. PATENT DOCUMENTS

| 4,252,122 | 2/1981 | Halvorsen . |
| 5,059,186 | 10/1991 | Yamamoto et al. . |
| 5,205,831 | 4/1993 | Ryan et al. . |
| 5,269,764 | 12/1993 | Vetter et al. . |

FOREIGN PATENT DOCUMENTS

| 0267584 | 5/1988 | European Pat. Off. . |
| 0336903 | 10/1989 | European Pat. Off. . |
| 53-44870 | 10/1978 | Japan . |
| 2-9824 | 3/1990 | Japan . |
| 3-37642 | 8/1991 | Japan . |
| 4-8918 | 3/1992 | Japan . |
| 4-193182 | 7/1992 | Japan . |

*Primary Examiner*—Corrine M. McDermott
*Assistant Examiner*—N. Kent Gring
*Attorney, Agent, or Firm*—Burns, Doane, Swecker & Mathis, LLP

[57] ABSTRACT

A connector has an instrument insertion passage which is provided with a seal member made from an elastic member formed with a seal member passage having a narrowed portion. When a knob is grasped and turned clockwise to turn a control body, the control body is forced into the connector and abuts the seal member causing the seal member to deform so as to reduce the inner diameter of the narrowed portion of the seal member, thereby enabling an instrument to be held by the narrowed portion in a fluid-tight manner which allows the instrument to be slidable through the connector. Also, by turning the control body further into the connector, the deformation of the seal member can be increased to cause the narrowed portion to fix the instrument in place in a manner that prevents the instrument from being slid through the connector 1.

19 Claims, 8 Drawing Sheets

CONNECTOR

BACKGROUND OF THE INVENTION

1. Field of the Invention

The present invention relates to a connector for slidably holding an instrument which is used by being inserted into a tube-shaped body in fluid-tight seal condition with the inside of the tube-shaped body, and in particular relates to a connector which is to be connected to a base end portion of a tube-shaped body such as a guide catheter to be inserted into a body, for slidably holding an instrument such as a balloon catheter or a guide wire to be inserted into the tube-shaped body in fluid-tight seal condition with the inside of the tube-shaped body.

2. Description of the Background Art

Up to now, when carrying out medical treatments on stenosis portion of blood vessels caused by arteriosclerosis or the like, Percutaneous Transluminal Coronary Angioplasty (PTCA) is adopted as the typical method of angioplasty. The PTCA is comprised of the steps of inserting a catheter equipped with a dilator such as a balloon at its tip into the stenosis portion of the blood vessel and inflating the dilator so as to dilate the stenosis portion of the blood vessel, thereby improving blood flow at the distal side thereof. During such surgical procedure, before the catheter equipped with the dilator is inserted into the blood vessel, a guide catheter which is used for guiding the dilator-equipped catheter toward the position of the stenosis portion is inserted and then held in place within the blood vessel. At such time, a Y-shaped connector is usually used, which is connected to the base end of the guide catheter before insertion of the dilator-equipped catheter.

As disclosed, for example, in Japanese Utility Model Publications No. 53-44870 and 4-8918, the known Y-shaped connector is composed of a connector body having an insertion passage extending in an axial direction thereof, a seal member formed of an elastic cylindrical body (O-ring) and a control body which is fitted or screwed to the connector body and which is used to change the inner diameter of the seal member by changing the shape of the seal member from the outside of the connector body. Thus, by screwing the control body into the connector body, the resulting pressure causes the seal member to change its shape, and this enables to hold the dilator-equipped catheter passing through the seal member under fluid-tight condition with the inside of the guide catheter.

However, the seal members of these kinds of prior art connectors have a simple cylindrical shape with a predetermined fixed inner diameter that is larger than the outer diameter of the dilator-equipped catheter. Therefore, if the dilator-equipped catheter is slid within the seal member without a complete pressure being applied to the seal member, blood that has flowed due to blood pressure into the inside of the connector will leak out through the spacing between the seal member and the dilator-equipped catheter. On the other hand, if the control body is used to constrict the seal member and thereby reduce the inner diameter thereof in order to prevent such leakage of blood, a major portion of the inner surface of the seal member is forced into pressurized contact with the catheter passing therethrough, resulting in an increase in the sliding resistance for the dilator-equipped catheter, which then makes it difficult to carry out operations with the dilator-equipped catheter. Furthermore, if the constricting force applied onto the dilator-equipped catheter due to the constriction of the seal member is too high, or if the surface contact area between the seal member and the dilator-equipped catheter is too large, there are cases that the dilator-equipped catheter would be damaged and therefore the connector can not be used.

Accordingly, there has been much difficulty in trying to make adjustments to the prior art connectors having a cylindrical seal member with a fixed inner diameter in order to achieve satisfactory results with regards to both fluid-tight seals and slidability of an instrument such as a catheter passing through the seal member.

SUMMARY OF THE INVENTION

Therefore, in order to overcome the problems mentioned above, it is an object of the present invention to provide a connector that does not cause any damage to an instrument passing therethrough and which can be reliably adjusted to achieve satisfactory results with regards to both fluid-tight seals and slidability of an instrument passing through the connector.

In order to achieve the object stated above, the connector according to the present invention comprises: a connector body having a tip portion which is adapted to be connected to or integrally formed with an end portion of a tube-shaped body, an end portion from which an instrument which is used by being inserted into the tube-shaped body is inserted, and an insertion passage which extends in an axial direction of the connector body so as to communicate the tip portion of the connector body with the end portion thereof; a seal member for slidably holding the instrument to be inserted into the insertion passage in a fluid-tight seal condition with the inside of the tube-shaped body, the seal member being formed from a substantially cylindrical elastic member disposed within the insertion passage of the connector body under the condition that radially outward deformation thereof is restricted, the seal member being formed with a seal member passage which is defined by an inner cylindrical surface of the seal member and whose axis is aligned with an axis of the insertion passage, and the seal member including a contact portion formed on a part of the inner surface, the contact portion being arranged in the close vicinity of the instrument being inserted so as to provide seal condition by being in contact with the instrument when the seal member is deformed by being compressed; and adjustment means for compressing the seal member so as to deform it, thereby providing the fluid-tight seal condition. In this connector, the contact portion is constituted into a narrowed portion formed in the seal member passage so as to have a reduced inner diameter, and the narrowed portion is formed by constituting the shape of the seal member passage so that the inner diameter thereof is gradually reduced from each of the end portions of the seal member passage to a substantially central portion thereof in such a manner that a cross section of the seal member passage along the axial direction thereof describes substantially two confronting parabola shapes, to form an annular protruding portion which protrudes toward the axis of the instrument insertion passage at the central portion of the seal member passage.

According to the connector having the above described structure, the following advantages can be obtained. Namely, since the connector according to the present invention includes the elastic seal member having the contact portion formed on the inner circumferential surface thereof which is arranged in the close vicinity of the instrument being inserted into the insertion passage and the adjustment means for compressing the seal member so as to deform it to provide the fluid-tight seal condition, the space between the contact portion and the instrument inserted therethrough is relatively narrow even in the condition that the seal member is not deformed without operating the adjustment means, which makes it difficult for fluids such as blood to leak through such space between the seal member and the instrument.

Further, when the adjustment means is operated to reduce the inner diameter of the seal member passage by deforming the seal member, the instrument then becomes held by the seal member under a fluid-tight seal condition being provided between the seal member and the instrument. In this state, since only the narrowest portion of the inner surface of the contact portion is in contact with the instrument, and since this contacting surface has a relatively small surface area, the instrument experiences very little frictional resistance when it is slid through the seal member. As a result, it becomes possible to prevent damage to the instrument while maintaining good slidability of the instrument through the seal member.

Moreover, even when the adjustment means is operated to further deform the seal member in order to hold the instrument with a pressure that prevents the instrument from being slid through the seal member, the instrument is still held only by the contact portion thereof. Accordingly, it is possible to fix the instrument in place with a minimum amount of pressure from the seal member, and this greatly reduces the risk of the instrument being damaged.

Preferably, the seal member is constituted so as to be deformable in response to the degree of the adjustment of the adjustment means at least between a first state in which the contact portion at least partially surrounds the instrument being inserted into the seal member through a slight gap with the instrument, a second state in which the contact portion is in contact with the instrument to provide the fluid-tight seal condition under the condition that the instrument is freely slidable through the seal member, and a third state in which the contact portion fixedly holds the instrument under fluid-tight seal condition.

Preferably, the narrowed portion of the seal member passage has an inner circumferential annular tip portion which defines the smallest inner diameter of the seal member passage, and the inner circumferential annular tip portion of the narrowed portion is adapted to contact with the inserted instrument such that the instrument is freely slidable, when the seal member is compressed and then deformed by the adjustment means.

Further, preferably, the contact portion is formed only on an end portion of the inner surface of the seal member in the longitudinal direction thereof.

Further, it is also preferred that the axial length "L" of the seal member and the outer diameter of the seal member "D" are determined so as to satisfy the relationship represented by the formula: $L \geq \frac{1}{3}D$. Preferably, the axial length "L" of the seal member and the outer diameter of the seal member "D" are determined so as to satisfy the relationship represented by the formula: $L \geq \frac{5}{6}D$. More preferably, the axial length "L" of the seal member and the outer diameter of the seal member "D" are determined so as to satisfy the relationship represented by the formula: $L \geq D$.

Furthermore, the seal member can be formed into a structure in which an annular recess is formed on the outer circumferential surface thereof at a position corresponding to the position where the contact portion is located. By constructing the seal member so, the seal member can be deformed with a less compressive force to obtain a fluid-tight seal by the contact portion. Further, the flexibility of the contact portion is increased and the slidability of the instrument and the damage preventing effect for the instrument are also improved.

Another aspect of the present invention is directed to a connector which comprises: a connector body having a tip portion which is adapted to be connected to or integrally formed with an end portion of a tube-shaped body, an end portion from which an instrument which is used by being inserted into the tube-shaped body is inserted, and an insertion passage which extends in an axial direction of the connector body so as to communicate the tip portion of the connector body with the end portion thereof; a seal member for slidably holding the instrument to be inserted into the insertion passage in a fluid-tight seal condition with the inside of the tube-shaped body, the seal member being formed from a substantially cylindrical elastic member disposed within the insertion passage of the connector body under the condition that radially outward deformation thereof is restricted, the seal member being formed with a seal member passage which is defined by an inner cylindrical surface of the seal member and whose axis is aligned with an axis of the insertion passage, and the seal member including a contact portion formed on a part of the inner surface, the contact portion being arranged in the close vicinity of the instrument being inserted so as to provide seal condition by being in contact with the instrument when the seal member is deformed by being compressed, in which the axial length "L" of the seal member and the outer diameter of the seal member "D" are determined so as to satisfy the relationship represented by the formula: $L \geq \frac{1}{3}D$; and adjustment means for compressing the seal member so as to deform it, thereby providing the fluid-tight seal condition.

Preferably, the axial length "L" of the seal member and the outer diameter of the seal member "D" are determined so as to satisfy the relationship represented by the formula: $L \geq \frac{5}{6}D$. Further, more preferably, the axial length "L" of the seal member and the outer diameter of the seal member "D" are determined so as to satisfy the relationship represented by the formula: $L \geq D$.

By constructing the shape and the size of the seal member in this way, when the seal member is compressed and deformed, it is possible to obtain a large deformation in the contact portion, thus leading to an improved seal effect and an improved slidability of the insturment. Further, damage preventing effect is also improved.

Other aspect of the present invention is directed to a connector which comprises: a connector body having a tip portion which is adapted to be connected to or integrally formed with an end portion of a tube-shaped body, an end portion from which an instrument which is used by being inserted into the tube-shaped body is inserted, and an insertion passage which extends in an axial direction of the connector body so as to communicate the tip portion of the connector body with the end portion thereof; a seal member for slidably holding the instrument to be inserted into the insertion passage in a fluid-tight seal condition with the inside of the tube-shaped body, the seal member being formed from a substantially cylindrical elastic member disposed within the insertion passage of the connector body under the condition that radially outward deformation thereof is restricted, the seal member being formed with a seal member passage which is defined by an inner cylindrical surface of the seal member and whose axis is aligned with an axis of the insertion passage, and the seal member including a contact portion formed on a part of the inner surface, the contact portion being arranged in the close vicinity of the instrument being inserted so as to provide seal condition by being in contact with the instrument when the seal member is deformed by being compressed; and adjustment means for compressing the seal member so as to deform it, thereby providing the fluid-tight seal condition, the adjustment means including a tip portion having an end surface which abuts on the seal member, and said adjustment means being adapted not to contact the inner surface of the passage of the seal member when the seal member is compressed and then deformed by the adjusting means.

By constructing the seal member and the adjusting member in this way, the seal member can be deformed uniformly and reliably, because the radial and inward deformation of the seal member will not be interfered with the adjusting means. As a result, it is possible to avoid that the instrument being inserted is damaged by the uneven deformation of the seal member, while maintaining the seal effect and the good slidability.

Yet another aspect of the present invention is directed to a connector which comprises: a connector body having a tip portion which is adapted to be connected to or integrally formed with an end portion of a tube-shaped body, an end portion from which an instrument which is used by being inserted into the tube-shaped body is inserted, and an insertion passage which extends in an axial direction of the connector body so as to communicate the tip portion of the connector body with the end portion thereof, the insertion passage having at least a large diameter portion at a base side thereof and a small diameter portion at a tip side thereof, and a step portion being formed between these portions; a seal member for slidably holding the instrument to be inserted into the insertion passage in a fluid-tight seal condition with the inside of the tube-shaped body, the seal member being formed from a substantially cylindrical elastic member disposed within the large diameter portion of the insertion passage of the connector body under the condition that radially outward deformation thereof is restricted, the seal member being formed with a seal member passage whose axis is aligned with an axis of the insertion passage which is defined by an inner cylindrical surface of the seal member, and the seal member including a contact portion formed on a part of the inner surface, the contact portion being arranged in the close vicinity of the instrument being inserted so as to provide seal condition by being in contact with the instrument when the seal member is deformed by being compressed, wherein the inner diameter of the seal member passage at the tip end thereof is the identical to that of the small diameter portion of the insertion passage so as to form a continuous inner circumferential surface at a Joint section between the seal member passage and the small diameter portion of the insertion passage; and adjustment means for compressing the seal member so as to deform it, thereby providing the fluid-tight seal condition.

According to this aspect of the present invention, it is possible to prevent tiny bubbles from remaining around the joint section. That is to say, such bubbles can be easily removed.

Yet another aspect of the present invention is also directed to a seal member used in a connector which is used by being inserted into a tube-shaped body in a fluid-tight seal condition with the inside of the tube. The seal member being disposed within an instrument insertion passage formed in the connector so as to be able to slidably hold an instrument being inserted into the instrument insertion passage in a fluid-tight seal manner. The seal member is formed into a roughly cylindrical shape having a certain length along the longitudinal direction of the instrument insertion passage and a seal member passage, and the seal member including a contact portion formed on a part of an inner surface defining the seal member passage, the contact portion being arranged in the close vicinity of the instrument being inserted so as to provide a fluid-tight seal condition by being in contact with the instrument when the seal member is deformed by being compressed. Further, the seal member is adapted to be deformed when a force is applied from outside, wherein the seal member is deformable in response to the degree of the adjustment of the adjustment means at least between a first state in which the contact portion surrounds the instrument being inserted into the seal member through a slight gap with the instrument, a second state in which the contact portion is in contact with the instrument to provide the fluid-tight seal condition under the condition that the instrument is freely slidable through the seal member, and a third state in which the contact portion fixedly holds the instrument in a fluid-tight seal condition, and wherein the axial length "L" of said seal member and the outer diameter of said seal member "D" are determined so as to satisfy the relationship represented by the formula: $L \geq \frac{1}{3}D$.

Other objects, structures and advantages of the present invention will be more apparent when taken in conjunction with the appended drawings.

DETAILED DESCRIPTION OF THE PREFERRED EMBODIMENTS

With reference to the drawings, a detailed description will now be given below for the preferred embodiments of the present invention.

Figure 1:
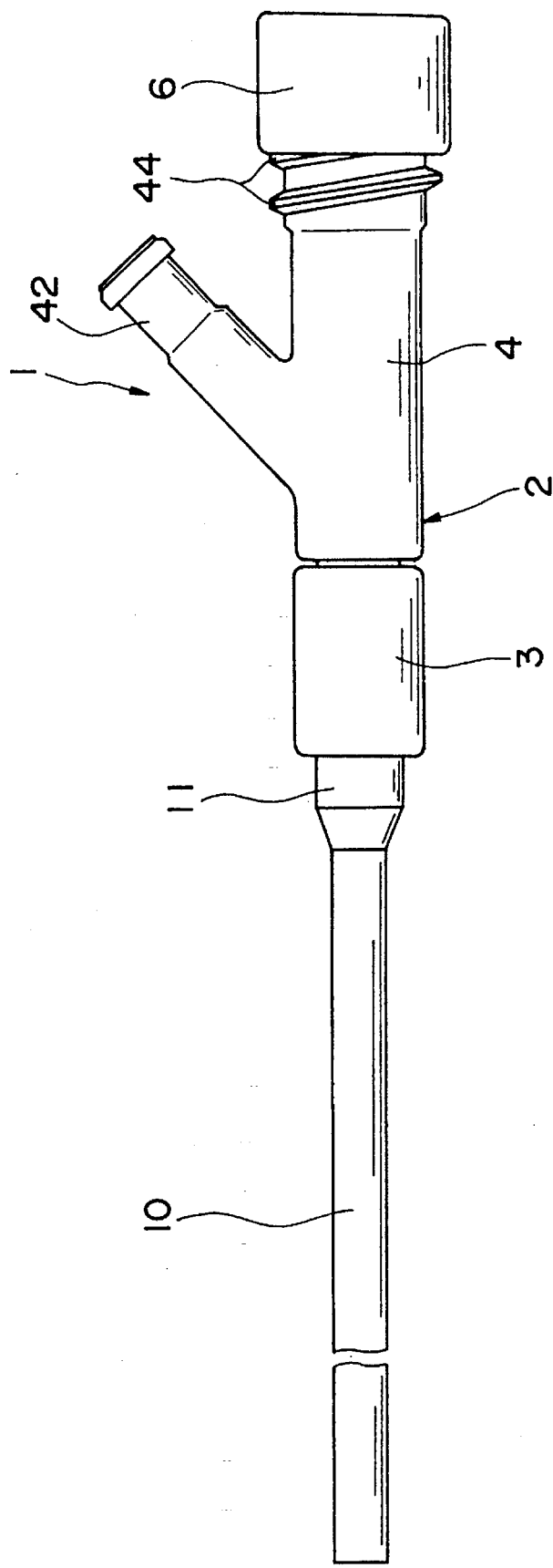
FIG. 1 is a top plan view of an embodiment of a connector according to the present invention.
Figure 2:
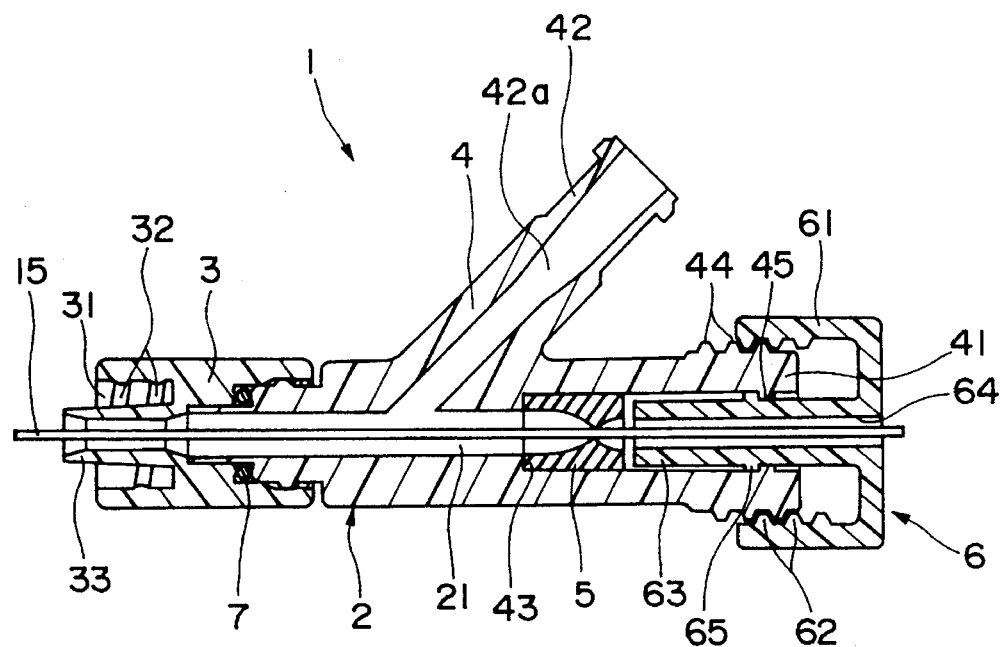
FIG. 2 is a vertical cross-sectional view of the connector shown in FIG. 1.
Figure 3:
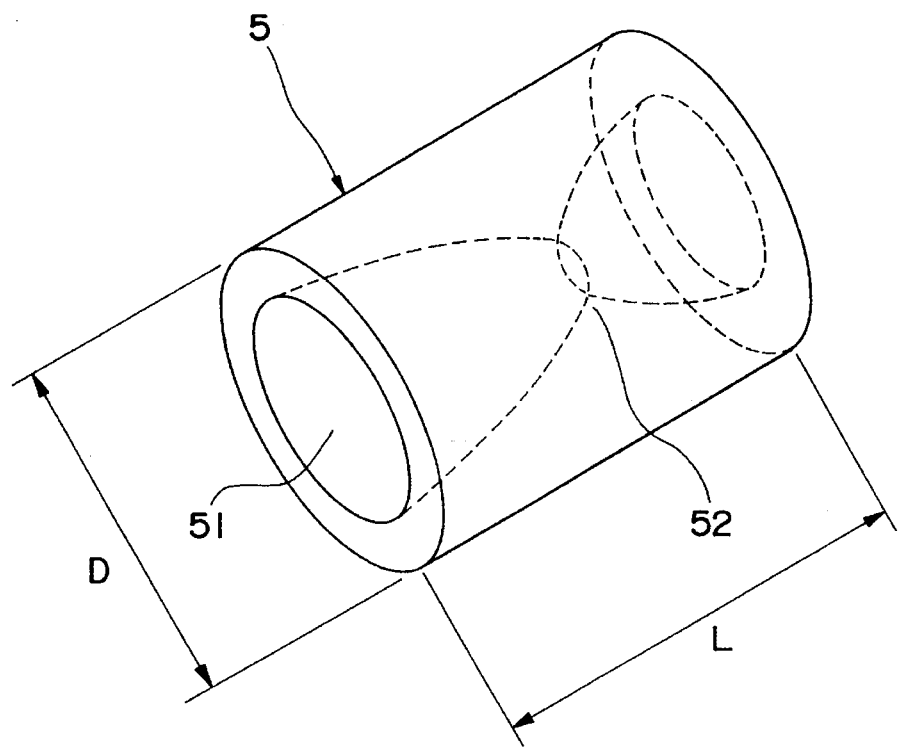
FIG. 3 is a perspective view of the seal member shown in FIG. 2.
Figure 4A:
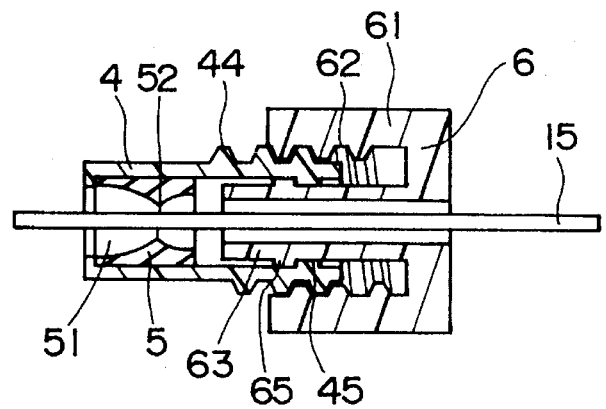
FIGS. 4 (A) (B) (C) (D) are a series of cross-sectional views illustrating the operation of a control body and a seal member.
Figure 4B:
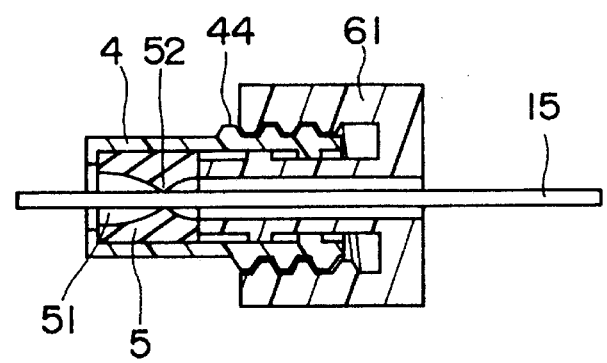
Figure 4C:
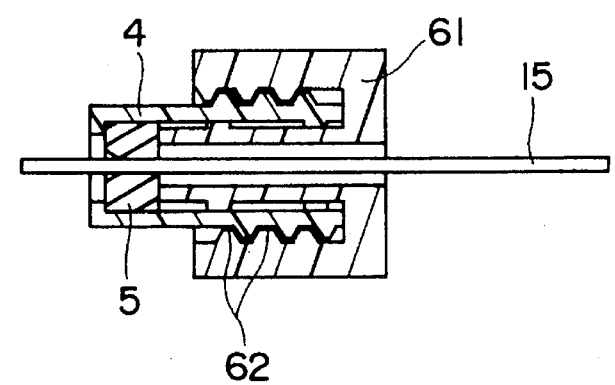
Figure 4D:
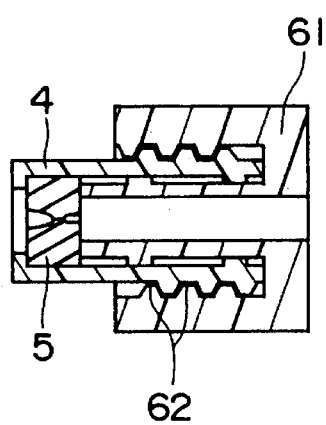
Figure 5A:
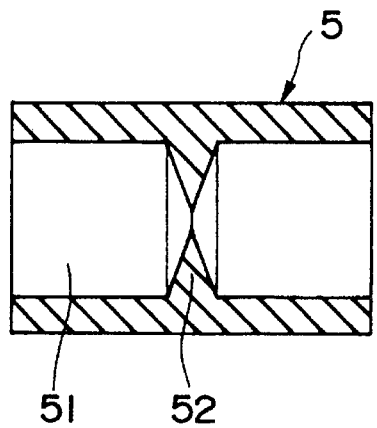
FIGS. 5 (A) (B) (C) (D) (E) (F) are cross-sectional views of modifications of the seal member shown in FIG. 4.
Figure 5B:
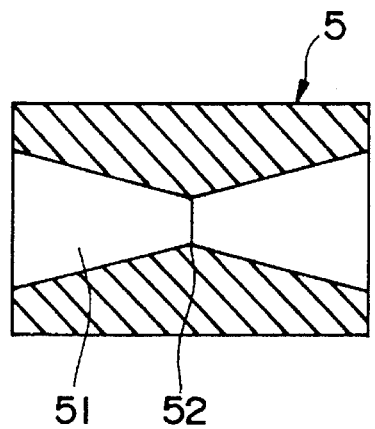
Figure 5C:
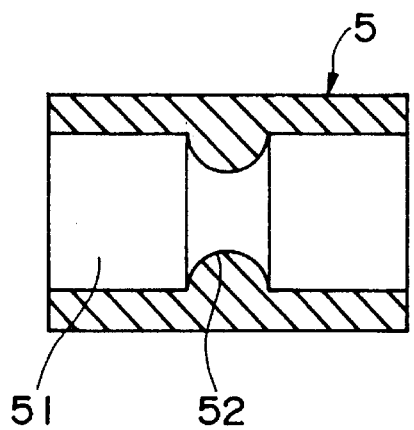
Figure 5D:
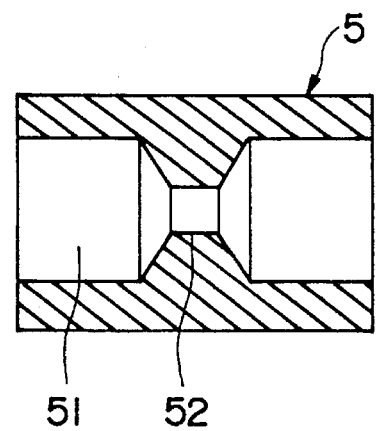
Figure 5E:
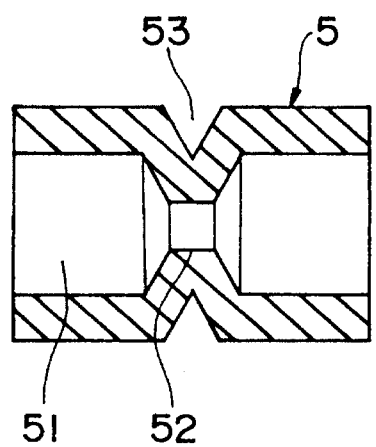
Figure 5F:
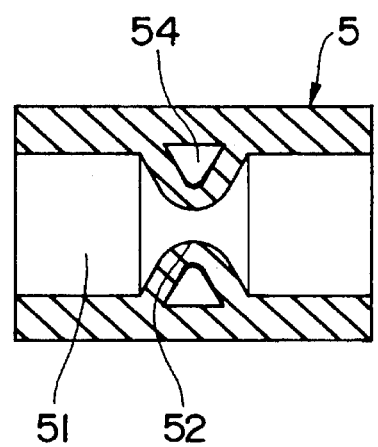

FIG. 1 is a top plan view showing an embodiment of a connector according to the present invention adapted for use as a Y-shaped connector for PTCA use, FIG. 2 is a vertical cross-sectional view of the connector shown in FIG. 1, and FIG. 3 is a perspective view or the seal member shown in FIG. 2. Now, in the descriptions to follow below, the right side and left side of the connector shown in FIGS. 1 and 2 will be defined as the base end and the tip end, respectively.

A connector 1 according to the present invention comprises a connector body 2 which is, at its tip end portion, adapted to be connected to a guide catheter 10 for guiding an instrument such as a dilator-equipped catheter to a position of an inlet port of a coronary arteries, and a control body 6 provided at the base end portion 41 of the connector body 2 for compressing and deforming a seal member 5 insertedly disposed inside the connector body 2. In this embodiment shown in the drawings, the guide catheter 10 is connected to the connector body 2 by means of a connecting device 11.

As shown in FIG. 2, the connector body 2 is composed of a cylindrical member 3 and a cylindrical member 4 which is fittedly coupled with the cylindrical member 3 under fluid-tight condition through an O-ring 7.

The tip end portion of the cylindrical member 3 is constituted as a connecting portion 31 for connecting the guide catheter 10. This connecting portion 31 comprises a concave portion having an internal thread 32 and a protruding portion 33 which protrudes out of the center of the concave portion. Thus, when the guide catheter 10 is connected to the connector 1 via the connecting device 11, the protruding portion 33 of the connecting portion 31 is first inserted into the base end of the internal cavity of the guide catheter 10, and then the external thread (not shown) of the connecting device 11 is screwed into the internal thread 32 of the connecting portion 31, thereby connecting the catheter 10 to the connector 1 by means of the connecting device 11.

The cylindrical member 4 is formed into a Y-shape so as to have a branched section with an end portion 42, so that the cylindrical member 4 has the end portion 42 in addition to the base end portion 41 described above. In each of these end portions 41 and 42, there is formed an opening respectively. The opening formed in the base end portion 41 serves as an instrument introducing port for introducing an instrument 15 (for example, the above-mentioned dilator-equipped catheter) which is used by being inserted into the guide catheter, into the connector 1. The opening formed in the end portion 42 serves as injecting port for injecting a contrast medium into the blood vessel through the path of the guide catheter 10 in order to confirm whether the blood flow has been improved through a stenosis portion of the blood vessel after such portion has undergone dilation. For constructing the cylindrical member 3 and cylindrical member 4, the preferred choice of materials are thermoplastic resins such as polycarbonate, polyamide, polysulfone, polyarylate, methacrylate-butylene-styrene copolymers and the like. With regard to the cylindrical member 4, a transparent material is preferably used for ensuring visibility of the inside thereof.

In the connector body 2 composed of the cylindrical members 3 and 4, there is formed an instrument insertion passage 21 which runs through the inside of the connector body 2 and extends from the protruding portion 33 of the cylindrical member 3 to the base end portion 41 of the cylindrical member 4 along the axis of the connector body 2. The above described instrument 15 such as a dilator-equipped catheter is inserted into the guide catheter 10 through the instrument insertion passage 21. Moreover, the instrument insertion passage 21 communicates with the opening of the base end portion 41 and the opening of the end portion 42 of the branched section of the cylindrical member 4.

Furthermore, a portion of the instrument insertion passage 21 at a position which lies toward the base end portion 41 and away from the position where the branched section is formed, has an enlarged inner diameter in comparison with that of the remaining portion of the instrument insertion passage 21 (hereinbelow, the remaining portion is referred as "small diameter portion"), so that a step portion 43 having a radial end surface is defined at the boundary section between the portions.

Formed on the outside of the base end portion 41 of the cylindrical member 4 is an external thread 44. This external thread 44 mates with an internal thread 62 formed in the control body 6 to allow the control body 6 to be screwed to the cylindrical member 4. Furthermore, formed inside the cylindrical member 4 in the vicinity of the base end of the instrument insertion passage 21 is a ring-shaped protruding portion 45 which protrudes toward the longitudinal axis of the instrument insertion passage 21.

In the enlarged inner diameter section of the instrument insertion passage 21, there is disposed a substantially cylindrical seal member 5 that serves as a seal means under the condition that one end surface of the cylindrical seal member 5 is in contact with the end surface of the step portion 43. This seal member 5 is formed of an elastic material. Axially formed in the seal member 5 is a seal member passage 51 through which the instrument such as a dilator-equipped catheter is adapted to pass. On the inner circumferential surface of the seal member which defines the seal member passage 51, there is integrally formed a contact portion which is adapted to contact with the instrument being inserted through the passage 51 to provide a fluid-tight seal when the seal member 5 is compressed and then deformed. In this embodiment, there is formed a narrowed portion (a small diameter portion) 52 at a part of the inner circumferential of the seal member 5 in the axial direction thereof, of which inner diameter is reduced in comparison with other portion. In more details, as shown in FIG. 3, the seal member passage 51 is formed such that the inner diameter of the passage 51 gradually decreases from both ends of the seal member until reaching a minimum diameter portion in the vicinity of the middle of the elastic member so as to describe substantially two confronting parabola shapes in cross section, respectively. As a result, at a substantially central portion of the seal member passage 51, there is formed a ring-shaped protruding portion which protrudes toward the longitudinal axis of the passage, and thus formed protruding portion forms the narrowed portion 52.

In this regard, it should be noted that the inner diameter of the seal member passage 51 at the tip end thereof is substantially identical to that of the small diameter portion of the insertion passage 21 so as to form a continuous inner circumferential surface at a Joint section between the seal member passage 51 and the small diameter portion of the insertion passage 21. This results in the advantage that bubbles can be prevented from remaining within the seal member passage 51.

When the control body 6 is not being used to change the shape of the seal member 5, the diameter of the narrowest part of the narrowed portion 52, namely the smallest diameter of the passage of the seal member 5, is slightly larger than the outer diameter of the instrument 15. Preferably, it lies within the range of 0.8 to 2.0 times the outer diameter of the instrument 15, and preferably lies within the range of 1.1 to 1.5 times the outer diameter of the instrument 15, and more preferably within the range of 1.2 to 1.5 times the outer diameter of the instrument. In this way, even when no compressing force is applied to the seal member 5 to change its shape, namely, even when the seal member 5 is in a released state or the seal member 5 is slightly pressed with a small force, it is possible to effectively prevent the leakage of fluid and the like from the space between the instrument 15 and the seal member 5.

As for the length of the seal member 5, there is no particular restriction, but in order for the seal member 5 to be able to maintain a fixed pressure on the instrument 15 when it is compressed and then deformed, the axial length of the seal member (L) should be restricted to lie within the range of 2.0 mm–7.0 mm, and preferably 5.0 mm–7.0 mm. Furthermore, the outer diameter of the seal member 5 (D) should lie within the range of 3.0 mm–6.0 mm, and preferably 4.0 mm–6.0 mm, and the thickness thereof at the both end portions should lie within the range of 0.5 mm–1.5 mm, and preferably 0.7 mm–1.0 mm.

The seal member 5 may be constructed from various kinds of rubber, such as silicone rubber, fluoro rubber, isoprene rubber, natural rubber and the like; various kinds of resins, such as polyurethane, polyamide elastomer, polybutadiene, soft vinyl chloride and the like; or from a combination of two or more of such compounds. For reliably maintaining the diameter of the seal member 5, silicone is particularly preferred because its relatively constant physical properties enable it to be formed into shapes having accurate dimensions.

Furthermore, it is preferred that the seal member 5 be constructed from a transparent material. In this way, it makes it possible to visibly confirm a contact state between the seal member 5 and an instrument which is inserted through the seal member 5 and also makes it easy to detect the presence of air bubbles remaining in the instrument insertion passage.

Also, as shown in FIG. 2, the seal member 5 is provided inside the instrument insertion passage 21 so that the longitudinal axis of the seal member passage 51 of the seal member 5 is aligned with longitudinal axis of the instrument insertion passage 21. Further, as described above, the seal member 5 is disposed within the instrument insertion passage 5 such that the one end surface thereof is in contact with the end surface of the step portion 43. In this way, the seal member 5 is at very least prevented by the end surface of the step portion 43 from moving in the direction toward the cylindrical member 3. Further, the inner diameter of the seal member passage at the tip end thereof is identical to that of the small diameter portion of the insertion passage so as to form a continuous inner circumferential surface at a joint section between the seal member passage and the small diameter portion of the insertion passage. According to this construction, it is possible to prevent tiny bubbles from remaining around the joint section. That is to say, such bubbles can be easily removed. Moreover, the seal member 5 is disposed within the enlarged inner diameter portion of the instrument insertion passage 21 under the condition that radially no space exists around the outer surface thereof. Accordingly, expansion or deformation of the outer surface of the seal member 5 in the radial direction thereof is restricted by the inner surface of the cylindrical member 4 which defines the instrument insertion passage 21.

The control body 6 serving as the adjustment means includes a cup-shaped knob 61 to be screwed at the base end portion 41 of the connector body 2 and a cylindrical pushing portion 63 which is integrally formed on a central portion of a bottom surface of the cup-shaped knob 61 and which is inserted into the enlarged inner diameter portion of the instrument insertion passage 21. In the pushing portion 63, there is formed an opening which extends from the tip portion thereof and the base end portion thereof for allowing insertion of the instrument 15 such as a dilator-equipped catheter. The inside of the tip portion of the cup-shaped knob 61 is provided with the internal thread 62 which mates with the external thread 44 formed on the base end portion of the cylindrical member 4. Therefore, when the cup-shaped knob 61 is grasped and then rotated in the clockwise direction when viewed from the side of the base end portion 41 of the connector body 2, the cup-shaped knob 61 is screwed with rotating toward the tip portion of the connector body 2. As a result, the pushing portion 63 integrally formed with the cup-shaped knob 61 is also forwardly inserted into the instrument insertion passage 21 with rotating. When the pushing portion 63 is further inserted into the instrument insertion passage 21, the tip of the pushing portion is brought into abutting with the seal member 5 of which movement is restricted by the end surface of the step portion 43 and the inner surface of the cylindrical member 4 which defines the instrument insertion passage 21, to compress and then deforms it in such a manner that the diameter of the passage 51 of the seal member 5 is reduced. On the other hand, when the cup-shaped knob 61 is rotated in the counterclockwise direction, the cylindrical pushing portion 63 is moved apart from the seal member 5 and then releases the compressed deformation of the seal member 5.

FIGS. 4 (A) (B) (C) (D) are a series of cross-sectional views showing a section of the connector in the vicinity of the seal member 5 which illustrate the use of the control body 6 in decreasing the inner diameter of the seal member 5.

In FIG. 4 (A), an instrument 15 such as a dilator-equipped catheter is shown as having been inserted into the instrument insertion passage 21, in which the pushing portion 63 of the control body 6 is positioned so as to be applying no compressing force on the seal member 5. In this state, the instrument 15 is able to slide without any resistance from the seal member 5. When the connector 1 is in the state described above, only a narrow space is formed between the narrowed portion 52 of the seal member 5 and the outer surface of the instrument 15 because the diametrical size of the narrowed portion 52 of the seal member 5 is set to be slightly larger than the outer diameter of the instrument 15, thereby making it possible to reduce the amount of blood that might leak out through such space as small as possible.

FIG. 4 (B) shows the next state after that shown in FIG. 4 (A), in which the cup-shaped knob 61 of the control body 6 has been rotated by grasping it in the clockwise direction when viewed from the base end 41 of the connector body 2 to move the pushing portion 63 of the control body 6 for a prescribed distance toward the tip end of the connector 1 so that the pushing portion 63 of the control body 6 presses against the seal member 5. In this state, the tip of the pushing portion 63 of the control body 6 pushes the seal member 5 from the base end side thereof to deform it, thereby reducing the inner diameter of the seal member 5, which in turn causes the inner surface of the narrowed portion 52 (that is, the inner surface of the circumferential tip portion of the narrowed portion) to make contact with the instrument 15 in such way that virtually no space lies between the narrowed portion 52 and the instrument 15. In other word, the inner circumferential portion of the narrowed portion 52 is in line-to-surface contact with the outer surface of the instrument 15. In this way, the seal member 5 is able to slidably hold the instrument 15 and maintain a fluid-tight seal around the instrument 15.

Now, when the seal member 5 and the instrument 15 are in the state depicted in FIG. 4 (B), only a small portion of the inner surface of the seal member 5 but the entire inner surface of the passage 51 of the seal member 5 is in line-to-surface contact with the instrument 15, namely the narrowest part of the narrowed portion 52. Since this contacting surface has a relatively small surface area, the instrument 15 experiences very little frictional resistance when it is slid through the seal member 5. As a result, if the control body 6 is fixed at this position, the instrument 15 will have good slidability through the seal member 5 with a fluid-tight seal being maintained between the instrument 15 and the seal member 5.

FIG. 4 (C) shows the next state after that shown in FIG. 4 (B), in which the cup-shaped knob 61 has been rotated further in the clockwise direction to insert the pushing portion 63 of the control body 6 into the instrument insertion passage 21 further in the direction of the tip end of the connector 1. In this state, the pushing portion 63 of the control body 6 further compresses the seal member 5 (in comparison to the state shown in FIG. 4 (B)), resulting in a greater degree of deformation of the seal member 5. Furthermore, the surface area of the narrowed portion 52 which is in contact with the instrument 15 becomes larger than the surface area of the narrowed portion 52 which is in contact with the instrument 15 for the situation depicted in FIG. 4 (B), and this results in the instrument 15 being held in a fixed position that does not enable the instrument 15 to be slid through the seal member 5. Furthermore, in this state, only a portion of the inner surface of the seal member 5 is in contact with the instrument 15, namely, only the deformed narrowed portion 52, but the entire inner surface of the passage 51 of the seal member 51, is in contact with the instrument 15. Otherwise, the seal member 5 is tightly fitted onto the instrument 15 under the condition that distribution of the compressing force becomes maximum at the narrowed portion 52. Accordingly, it is possible to fix the instrument 15 in place with a minimum amount of compressing force from the seal member 5, and this greatly reduces the risk of the instrument 15 being damaged.

FIG. 4 (D) shows the state in which the pushing portion 63 of the control body 6 is in the same position as that depicted in FIG. 4 (C) but with no instrument being inserted through the seal member 5. In this state, the seal member 5 is compressed in such a way that causes the narrowed portion 52 to shut off the passage 51, and this makes it possible to reliably prevent blood from leaking out of the base end of the connector 1.

Formed on a central portion of the outer circumferential surface of the pushing portion 63 of the control body 6 is a ring-shaped engagement convex portion 65. This engagement convex portion 65 is adapted to be engaged with the ring shaped convex portion 45 positioned in the instrument insertion passage 21. As a result, the movement of the control body 6 toward the base end of the connector 1 is restricted in a way that prevents the control body 6 from being pulled out of the instrument insertion passage 21.

However, the convex portion 45 and the convex portion 65 need not be formed to run completely around the inner and outer circumferential surfaces of the cylindrical member 4 and the pushing portion 63 of the control body 6, respectively. Instead, it is also possible to provide a plurality of convex portions spaced a prescribed distance from each other at regular angular positions on the circumferential surfaces thereof.

In the embodiment illustrated in the drawings, the control body 6 is screwed to the cylindrical member 4 by means of the external thread 44 formed on the cylindrical member 4 and the internal thread 62 formed on the cup-shaped knob 61 of the control body 6. However, the present invention is not limited to this structure, and instead it is possible to employ other means to screw the control body 6 to the cylindrical member 4. For example, it is possible to provide an internal thread in the instrument passage 21 of the cylindrical member 4 and an external thread on the portion of the control body 6 which lies inserted in the instrument insertion passage 21. Furthermore, the structure of the adjustment means is not limited to the control body 6 illustrated in the drawings. For example, it is possible to employ a structure like that described in the above-mentioned Utility Model No. 53-44870, in which a separate compression member is provided for compressing the seal member 5. In such case, the seal member 5 is deformed indirectly by operating a control body 6. That is to say, in this case, the control body 6 causes the compression member to move in the longitudinal direction of the connector.

The seal member 5 according to the present invention is preferably formed into the structure shown in FIG. 3 in which the axial length "L" of the seal member 5 and the outer diameter "D" of the seal member 5 are set so as to satisfy the relationship represented by the formula $L \geq \frac{1}{3}D$, preferably $L \geq \frac{2}{3}D$, and more preferably $L \geq D$. By doing so, when the seal member 5 is compressed and deformed by the pushing portion 63, it is possible to obtain a large deformation of the narrowed portion 52 toward the longitudinal axis of the seal member 5. In other words, the change rate of the inner diameter of the narrowed portion 52 becomes large before and after the compressive force being applied. Therefore, it is possible to obtain the seal effect and the slidability of the instrument as described above and to prevent the instrument from being damaged. In particular, there is a case that the outer diameter of the instrument 15 is different from each other between the case that a catheter is used as the instrument and the case that a guide wire is used as the instrument. Further, there is also a case that the outer diameters of catheters are different from each other depending on the kinds of catheters. However, according to the present invention, the above effects can be realized in spite of the kinds of the catheters.

Furthermore, the shape of the narrowed portion 52 of the present invention is not limited to the shape illustrated in FIG. 3. Various shapes may be adapted for the narrowed portion 52 if they can apply pressure to the instrument passing through the seal member and then hold it when they are compressed and then deformed. For example, as shown in FIG. 5 (A), the narrowed portion 52 may be constructed from a ring-shaped protruding portion formed at substantially central portion of the circumferential inner surface of the passage 51 and having a rectangular cross section in the axial direction of the seal member. Further, as shown in FIG. 5 (B), the narrowed portion 52 may be formed into a protruding shape positioned at substantially central portion of the seal member passage 51 and protruding toward the longitudinal axis of the passage 51, in which the inner diameter of the passage 51 is decreased from each of the end portions of the passage 51 until reaching the central portion thereof in such a manner that each portion of the passage 51 forms a substantially conical shape, respectively. Furthermore, as shown in FIG. 5 (C), the narrowed portion 52 may be formed into a ring-shaped protruding portion formed at substantially central portion of the circumferential inner surface of the passage 51 and having a semi-circular shape in cross section along the axial direction. Moreover, as shown in FIG. 5 (D), the narrowed portion 52 may be formed into a ring-shaped protruding portion formed on substantially central portion of the circumferential inner surface of the passage 51 and having a substantially trapezoidal shape in cross section along the axial direction of the seal member.

According to other modifications, as shown in FIG. 5 (E), the seal member 5 can be formed into a structure in which an annular recess 53 is formed on the outer circumferential surface thereof at a position corresponding to the position where the narrowed portion 52 is located. Further, as shown in FIG. 5 (F), the seal member 5 can be formed into the structure in which a hollow space 54 is formed inside the narrowed portion 52. By providing the recess 53 or hollow space 54, the elasticity of the seal member 5 is increased. With this result, since the seal member 5 can be compressed and deformed easily with a small degree of compressive force, a large amount of deformation toward the central axis of the seal member 5 can be obtained. Further, in a case where the recess 53 or hollow space 54 is formed in the seal member, the flexibility of the narrowed portion 52 is increased, and the slidability and the damage preventing effect are further improved.

Among these modifications for the shape of the narrowed portion, the shape of the narrowed portion 52 of the first embodiment shown in FIGS. 2 to 4, that is the narrowed portion formed by the passage 51 of which inner diameter thereof steadily decreases from both ends until reaching a minimum diameter portion in the vicinity of the middle of the passage so as to describe a substantially parabola shape in cross section, respectively, is most preferable, since compressive force applied to the seal member 5 is surely transmitted to the smallest diameter portion (that is, the inner surface of the circumferential tip portion) of the narrowed portion 52.

Figures 6A, 6B:
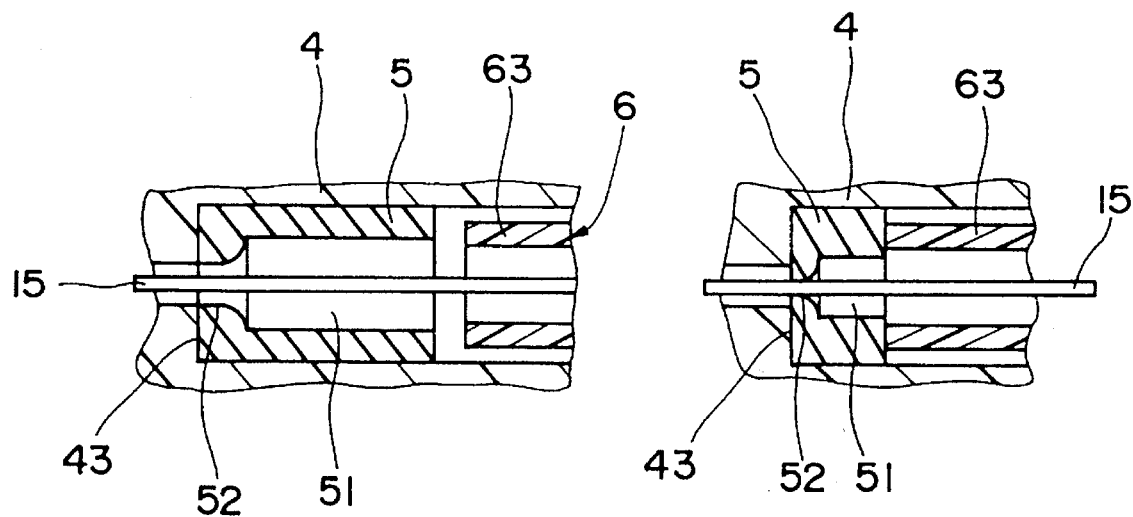
FIGS. 6 (A) (B) are cross-sectional views illustrating other embodiments of a seal member and a control body.

Alternatively, in the present invention, the position at which the narrowed portion 52 is formed is not limited to the central position of the passage 51. Instead, as shown in FIG. 6 (A), it is possible to form the narrowed portion at the end portion of the passage 51 on the side of the step portion 43. In this case, in the same manner as the above described embodiment, the seal member 5 is also deformed so as to reduce the inner diameter of the passage 51 as shown in FIG. 6 (B) when the seal member 5 is compressed by the control body 6, so that it is possible to compress and hold the instrument 15 with the narrowed portion 52. In this regard, it should be noted that shapes of the narrowed portion 52 in this embodiment can be modified as shown in FIGS. 5 (A)–(F).

Shapes of the seal member 5 according to the present invention is not limited to the cylindrical shapes described above with reference to the embodiments. Other shapes can be adopted if they can hold an instrument such as a dilator-equipped catheter in a fluid-tight seal manner when they are compressed and then deformed.

In these emebodiments, it is also possible to provide a plurality of regularly spaced contact portions 52 in the seal member 5 in a manner that does not give rise to a loss in slidability for an instrument. In this way, since the instrument 15 would be held under compression at a plurality of positions, the effectiveness of the fluid-tight seal provided by the present invention can be even further improved.

Hereinafter, descriptions are made with reference to a case where the connector 1 having the above described structure is used in carrying out a PTCA surgical procedure. In this case, first a guide catheter 10 is moved forward following a guide catheter guide wire that has been previously inserted into a blood vessel, and then a dilator-equipped catheter is being moved forward toward a desired position inside a blood vessel through the guide catheter 10 that has been previously inserted in the blood vessel. When carrying out these operations, the control body 6 is in the state shown in FIG. 4 (B). Therefore, it is possible to form a fluid-tight seal between the guide catheter 10 and the guide wire or between the guide catheter 10 and the dilator-equipped catheter without any damage being caused to either the guide wire or the dilator-equipped catheter. Further, in the case where either the guide wire or the dilator-equipped catheter is pulled out through the guide catheter 10, if the control body 6 is in the state shown in FIG. 4 (B), the guide wire and the dilator-equipped catheter can be pulled out smoothly without any blood leaking out from the connector 1. Furthermore, after the dilator-equipped catheter has been passed through the guide catheter 10 and reaches the desired position within the blood vessel where it is to be dilated, it is possible to fix the dilator-equipped catheter in place in a manner that does not cause any damage to the dilator-equipped catheter by moving the control body 6 to the state shown in FIG. 4 (C).

In the foregoings, the present invention and the embodiments thereof are explained with reference to the case where the present invention is applied to a Y-shaped connector for PTCA use. However, the present invention is not limited to the Y-shaped connector described above. Instead, it is possible to use the connector according to the present invention as connectors used when slidably holding medication delivering catheter, body fluid aspirating catheter or endoscope within a large diameter catheter which is used for introducing these catheters to desired sites within a body, when slidably holding forceps or fiber optics which is used by passing through an endoscope, or when connecting hollow needles to narrow-diameter tubes.

EXPERIMENTAL EXAMPLES

Hereinbelow, the present invention will now be described with reference to specific examples.

[CONNECTOR USED IN THE EXPERIMENTS]

A connector like the one illustrated in FIGS. 1 and 2 was prepared according to the specifications listed below:

(A) Material of Connector Body 2: polycarbonate (B) Position of Step portion 43: spaced 1.90 cm from the base end of the instrument insertion passage 21

(C) Inner Diameter of Instrument Insertion Passage 21: from the step portion 43 to the base end is 6.0 mm; and from the step portion 43 to the tip end is 4.0 mm (D) Material of Seal Member 5: silicone rubber (JIS hardness C 2123; 28)

(E) Length of Seal Member 5: 7.0 mm (F) Outer Diameter of Seal Member 5: 6.0 mm (G) Inner Diameter of Seal Member 5: 4.0 mm at the tip end; 2.5 mm at the base end; and 1.5 mm (4.5 Fr) at the narrowed portion 52

(H) Position of the narrowed portion: position of smallest diameter portion is 2.7 mm from the base end of the seal member 5

(I) Total Length of Control Body 6: 1.80 cm (J) Outer Diameter of Pushing Portion 63 of Control Body 6: 5.8 mm (K) Inner Diameter of Opening of Pushing Portion 63 of Control Body 6: 2.5 mm (identical to the size of the inner diameter of the passge of the seal member 5 at the base end thereof)

The connector prepared according to the above specifications was used in carrying out Experiment 1 and Experiment 2 described below.

[EXPERIMENT 1]

Measurements were made with regard to the relationship between the distance that the control body 6 pushes the seal member 5 and the smallest inner diameter of the narrowed portion 52 while the control body 6 was rotated in clockwise direction so as to cause it to move toward the tip end of the connector 1. The results of such measurements are shown in FIG. 7.

Figure 7:
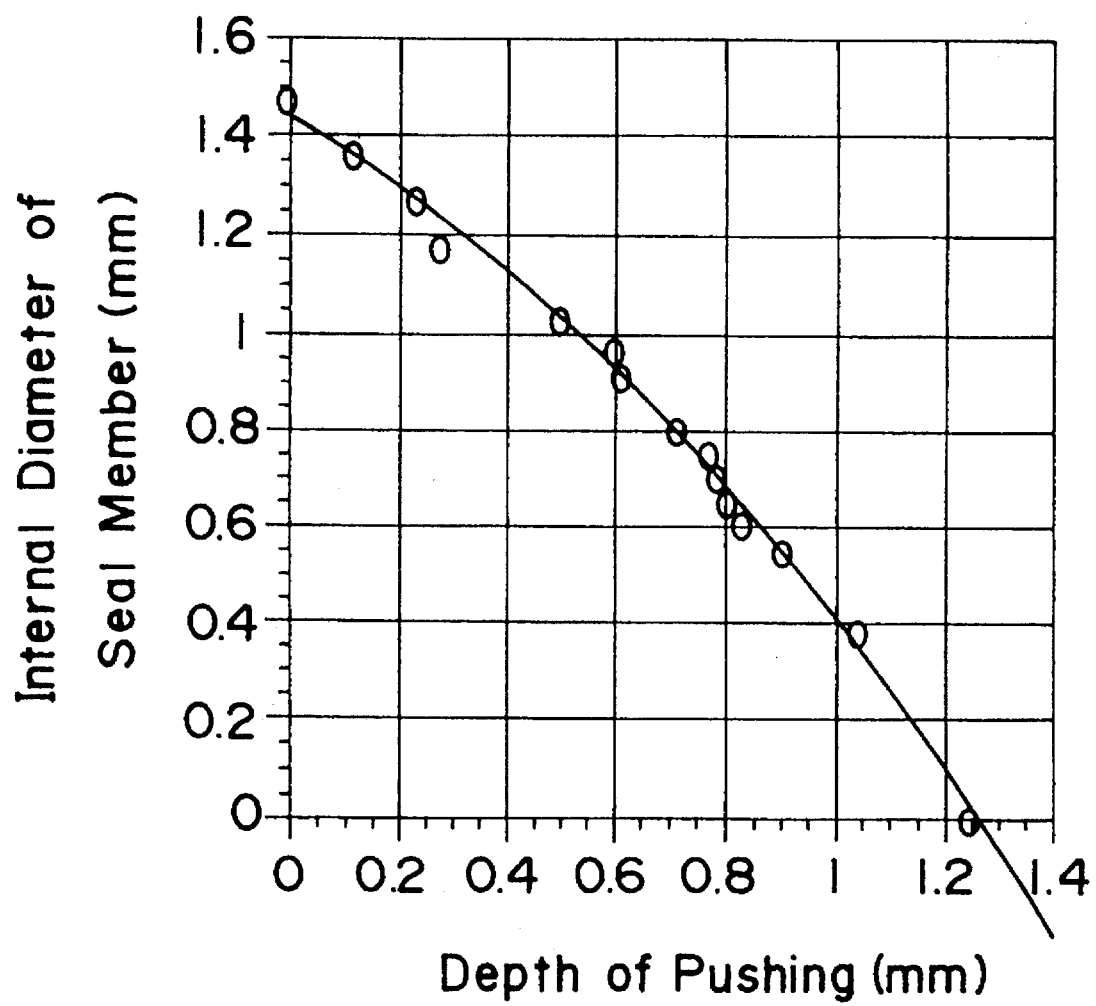
FIG. 7 is a graph of the change in inner diameter of the seal member in response to the amount of compression caused to the seal member by the control body.

As shown in FIG. 7, the smallest diameter of the seal member 5 decreases as the compression of the seal member 5 by the control body 6 increases.

[EXPERIMENT 2]

Stainless steel rods were prepared having outer diameters of 0.9 mm (2.7 Fr), 1.2 mm (3.6 Fr) and 1.5 mm (4.5 Fr). Then, with these rods inserted in the seal member in a fluid-tight manner, the measurements described below were carried out to determine the slidability of such rods.

[MEASUREMENT 1]

A tube was prepared having an outer diameter of 5.4 mm, an inner diameter of 2.5 mm and a total length of 52.0 cm. Then one end of the tube was connected in a fluid-tight manner to the connector of Example 1 via a connecting means 11 having the structure shown in FIG. 1, and the other end of the tube was closed off with a clamp to form a fluid-tight seal.

Next, in a state in which the control body 6 is positioned so as to cause no compression of the seal member 5, the tips of each of the 0.9 mm (2.7 Fr) and 1.2 mm outer diameter rods were inserted from the end 42 of the connector into the instrument insertion passage 21 so as to protrude into the inside of the tube. Then, the base end of the connector was connected to one port of a three-way seal member, and a syringe pump and a pressure gauge were connected, respectively, to the two remaining ports of the three-way seal member.

In this state, while water was being supplied by the syringe pump, the knob 61 was grasped and the control body 6 was turned to move it in the longitudinal direction of the connector in order to adjust the inner diameter of the passage 51 of the seal member 5. Then, the position of the tip portion of the control body 6 was recorded at the time when water at 1 atm leaked through the space between the seal member 5 and the rod inserted therethrough.

In this regard, it should be noted that because the outer diameter of the 1.5 mm (4.5 Fr) rod was the same as the smallest diameter of the seal member 5, the measurements described above were not carried out for the 1.5 mm rod.

After the above measurements were carried out, the Measurement 2 stage described below was carried out.

[MEASUREMENT 2]

Figure 8:
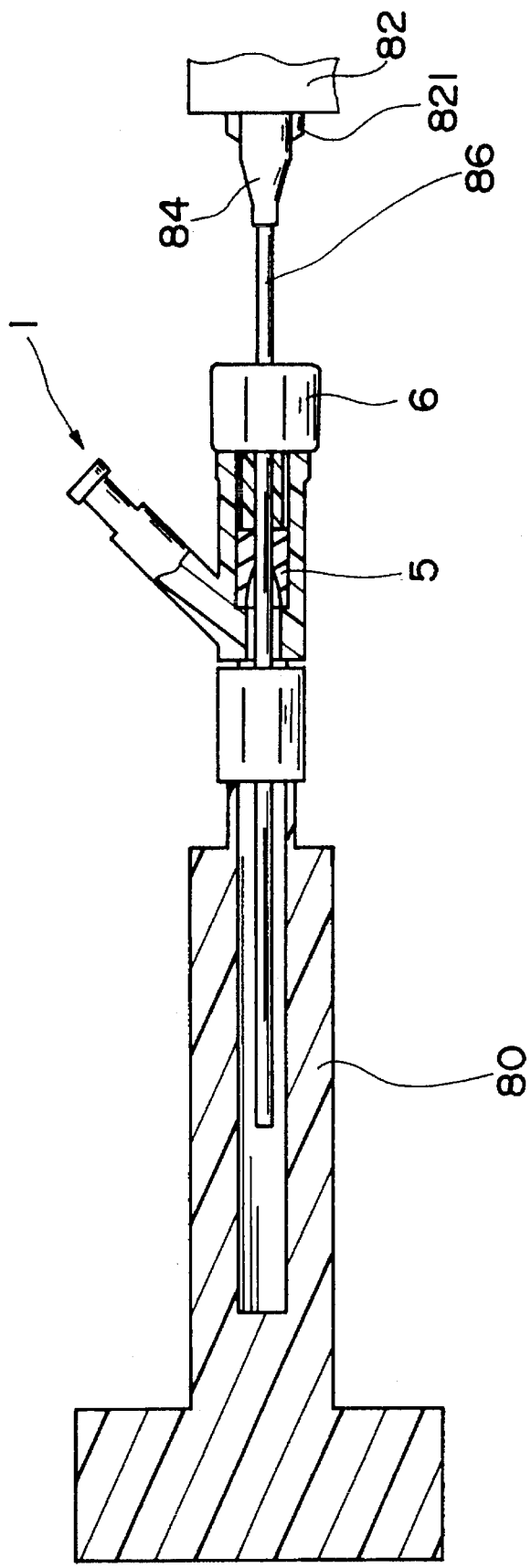
FIG. 8 is a front view showing an experimental apparatus and method for measuring sliding resistance.

As shown in FIG. 8, with the connector 1 of Example 1 fixed perpendicular to a base 80, each of the 0.9 mm, 1.2 mm and 1.5 mm rods 86 was inserted into the connector 1. For each such state, the control body 6 was moved to the previously recorded positions mentioned above (in the case of the 1.5 mm rod 86, the control body 6 was positioned so that no compression of the seal member 5 takes place) in order to reduce the inner diameter of the seal member 5. Then, the base end of each rod 86 was connected via a connecting means 84 to a mounting portion 821 of an autograph 82. One end of the connecting means 84 is constructed so as to be connectable to the base end of the rod 86 and the other end thereof is constructed so as to be connectable with the mounting portion 821 of the autograph 82.

On the other hand, in order to simulate conditions, water is poured from the opening of the end portion 42 to fill the instrument insertion passage 21 up to seal member 5.

In this state, the rod 86 was slid by the autograph 82 through the connector 1 and the resistance exerted onto the rod 88 during the sliding movement was measured. The conditions under which such sliding was carried out are indicated below.

[Sliding Conditions]

Sliding Stroke: 100 mm

Sliding Speed: 200 mm/min

Figure 9:
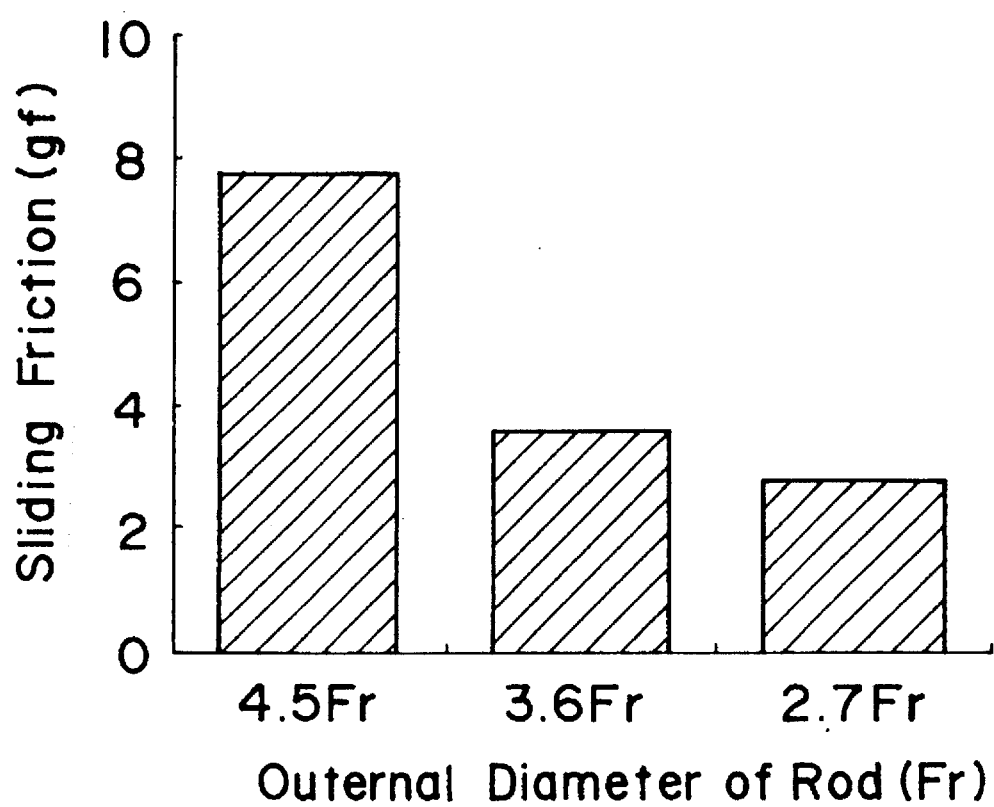
FIG. 9 is a bar graph showing the sliding resistance for the connector according to the present invention.

The resulting measurements are shown in FIG. 9. As made clear by the information shown in FIG. 9, in addition to maintaining a fluid-tight seal under pressure condition (i.e., at 1 atm) that is much higher than the highest blood pressure of a human body, the sliding resistance lies below 10 gf for all the rods 86. This data confirms that the connector according to the present invention makes it easy for a practioner to manipulate instruments inserted through the connector. Therefore, even when the connector according to the present invention is being used during a PTCA procedure under conditions in which no blood leaks out from the inside of the connector, it is still easy for the practioner to manipulate an instrument such as a dilator-equipped catheter.

As stated above, according to the present invention, it is possible to surely adjust the sealability of the seal member and the slidability of the instrument held by the seal member at the same time and satisfy the demands without any risk of damages of the instrument.

Finally, it should be noted that the present invention is not limited to the embodiments described above and the scope of the invention will be determined only by the following claims.

What is claimed is:

1. A connector, comprising:
   a connector body having a tip portion which is adapted to be connected to or integrally formed with an end portion of a tube-shaped body, an end portion from which an instrument which is used by being inserted into the tube-shaped body is inserted, and an insertion passage which extends in an axial direction of the connector body so as to communicate said tip portion of said connector body with said end portion thereof;
   a seal member for slidably holding said instrument in a fluid-tight seal condition with an inside of said tube-shaped body, said seal member being formed from a substantially cylindrical elastic member disposed within said insertion passage of said connector body under a condition such that radially outward deformation thereof is restricted, said seal member being formed with a seal member passage which is defined by an inner cylindrical surface of said seal member, the seal member passage having an axis that is aligned with an axis of said insertion passage, and said seal member including a contact portion formed on a part of said inner surface, said contact portion being arranged in close vicinity of said instrument so as to provide seal condition by being in contact with said instrument when said seal member is deformed by being compressed, wherein said contact portion is constituted into a narrowed portion formed in said seal member passage so as to have a reduced inner diameter, and said narrowed portion is formed by constituting a shape of said seal member passage so that the inner diameter thereof is gradually reduced until reaching a minimum diameter thereof; and adjustment means for compressing said seal member so as to deform it, thereby providing the fluid-tight seal condition, wherein said contact portion of said seal member is adapted to be deformed such that the contact area between the narrowed portion thereof and said instrument becomes larger as more compressive force is applied on said seal member by said adjustment means.

2. The connector as claimed in claim 1, wherein said seal member is deformable in response to the degree of the adjustment of said adjustment means at least between a first state in which said contact portion surrounds said instrument through a slight gap around said instrument, a second state in which said contact portion is in contact with said instrument to provide the fluid-tight seal condition under the condition that said instrument is freely slidable through said seal member, and a third state in which said contact portion fixedly holds said instrument under the fluid-tight seal condition.

3. The connector as claimed in claim 2, wherein said narrowed portion of said seal member passage has an inner circumferential annular tip portion which defines the smallest inner diameter of said seal member passage, and said inner circumferential annular tip portion of said narrowed portion is adapted to contact with said instrument such that said instrument is freely slidable, when said seal member is compressed and then deformed by said adjustment means.

4. The connector as claimed in claim 1, wherein said contact portion is formed only on an end portion of said inner surface of said seal member in a longitudinal direction thereof.

5. The connector as claimed in claim 1, wherein an axial length "L" of said seal member and an outer diameter "D" of said seal member satisfy a relationship: L≧D.

6. The connector as claimed in claim 1, wherein said seal member has an outer circumferential surface having an annular recess formed thereon, said recess being formed along the circumferential surface corresponding to a location of said contact portion.

7. The connector as claimed in claim 1, wherein said contact portion has a hollow space inside thereof.

8. A connector as claimed in claim 1, wherein an axial length "L" of said seal member and an outer diameter "D" of said seal member satisfy a relationship: L≧⅓D.

9. The connector as claimed in claim 1, wherein an axial length "L" of said seal member and an outer diameter "D" of said seal member satisfy a relationship: L≧⅝D.

10. The connector as claimed in claim 1, wherein an axial length "L" of said seal member and an outer diameter "D" of said seal member satisfy a relationship: L≧D.

11. A connector as claimed in claim 1, wherein said adjustment means includes a tip portion having an end surface which abuts on the seal member, said adjustment means adapted not to contact the inner surface of said passage of said seal member when said seal member is compressed and then deformed by said adjusting means.

12. The connector as claimed in claim 11, wherein said narrowed portion is formed from an annular protruding portion having a semi-circular cross section along the seal member passage axis, said protruding portion being formed on the inner circumferential surface of said seal member passage substantially at a central portion thereof.

13. The connector as claimed in claim 11, wherein said narrowed portion is formed from an annular protruding portion having a trapezoidal cross section along the seal member passage axis, said protruding portion being formed on the inner circumferential surface of said seal member passage substantially at a central portion thereof.

14. The connector as claimed in claim 1, wherein said narrowed portion is formed by constituting the shape of said seal member passage so that the inner diameter thereof is gradually reduced from each of the end portions of said seal member passage to a substantially central portion thereof in such a manner that a cross section of said seal member passage along the axial direction thereof describes substantially two confronting parabola shapes, to form an annular protruding portion which protrudes toward the axis of said insertion passage at the central portion of said seal member passage.

15. The connector as claimed in claim 1, wherein said narrowed portion is formed from an annular protruding portion having a triangular cross section along the seal member passage axis, and said protruding portion is formed on the inner surface of said seal member passage substantially at a central portion thereof.

16. The connector as claimed in claim 1, wherein said narrowed portion is formed by constituting said seal member passage so that the inner diameter thereof is reduced so as to form a substantially conical shape extending from each of the end portions of said seal member passage to form an annular protruding portion which protrudes toward the axis of said insertion passage at a substantially central portion of said seal member passage.

17. A connector as claimed in claim 1, wherein said insertion passage has at least a large diameter portion at a base side thereof and a small diameter portion at a tip side thereof, and the inner diameter of said seal member passage at a tip end thereof is identical to an inner diameter of the small diameter portion of said insertion passage so as to form a continuous inner circumferential surface at a joint section between said seal member passage and the small diameter portion of the insertion passage.

18. A connector as claimed in claim 1, wherein said seal member is formed into such a shape that a cross section of said seal member passage along the seal member passage axis describes substantially two confronting parabola shapes so as to form an annular protruding portion which protrudes toward the axis of said insertion passage at a central portion of said seal member passage.

19. A seal member used in a connector which is used by being inserted into a tube-shaped body in a fluid-tight seal condition with the inside of the tube, said seal member being disposed within an instrument insertion passage formed in the connector so as to be able to slidably hold an instrument being inserted into the instrument insertion passage in a fluid-tight seal manner, wherein:

said seal member being formed into a roughly cylindrical shape having a certain length along the longitudinal direction of said instrument insertion passage and a seal member passage, and said seal member including a contact portion formed on a part of an inner surface defining said seal member passage, said contact portion being arranged in the close vicinity of the instrument being inserted so as to provide a fluid-tight seal condition by being in contact with the instrument when said seal member is deformed by being compressed, wherein said contact portion is constituted into a narrowed portion formed in said seal member passage so as to have a reduced inner diameter, and the inner diameter of said narrowed portion is gradually reduced until reaching a minimum diameter portion thereof; and said seal member being adapted to be deformed when a force is applied from outside, wherein said seal member is deformable in response to the degree of the adjustment of said adjustment means at least between a first state in which said contact portion surrounds the instrument being inserted into said seal member through a slight gap with the instrument, a second state in which said contact portion is in contact with the instrument to provide the fluid-tight seal condition under the condition that the instrument is freely slidable through said seal member, and a third state in which said contact portion fixedly holds the instrument in a fluid-tight seal condition.

* * * * *

UNITED STATES PATENT AND TRADEMARK OFFICE
CERTIFICATE OF CORRECTION

PATENT NO. : 5,599,327
DATED : February 4, 1997
INVENTOR(S) : Michihiro SUGAHARA et al It is certified that error appears in the above-indentified patent and that said Letters Patent is hereby corrected as shown below:

In Column 3, line 58, delete "5/8" and insert -- 5/6 --.

In Column 7, line 56, delete "alone" and insert -- along --.

In Column 9, line 27, after "passage" and insert -- 21. --.

In Column 16, line 11, delete "88" and insert -- 86 --.

Signed and Sealed this

Twentieth Day of May, 1997

Attest:

BRUCE LEHMAN

Attesting Officer          Commissioner of Patents and Trademarks